United States Patent [19]
Van Der Schaaf et al.

[11] Patent Number: 5,912,376
[45] Date of Patent: Jun. 15, 1999

[54] PROCESS FOR THE PREPARATION OF CATALYSTS

[75] Inventors: Paul Adriaan Van Der Schaaf, Fribourg; Roman Kolly, Zumholz; Andreas Hafner, Laupen; Andreas Mühlebach, Belfaux, all of Switzerland

[73] Assignee: Ciba Specialty Chemicals Corporation, Tarrytown, N.Y.

[21] Appl. No.: 08/958,680

[22] Filed: Oct. 27, 1997

[30] Foreign Application Priority Data

Nov. 1, 1996 [CH] Switzerland ............... 270796

[51] Int. Cl.$^6$ ............... C07F 15/00; C07F 9/02
[52] U.S. Cl. ............... 556/22; 556/23; 556/136; 502/155
[58] Field of Search ............... 556/22, 23, 136

[56] References Cited

FOREIGN PATENT DOCUMENTS 9604289  7/1995  WIPO .
97/06185  2/1997  WIPO .

OTHER PUBLICATIONS

R.H. Grubbs, et al., Ring–Closing Metathesis and Related Process in Organic Synthesis, Acc Chem. Res. 1995, 28. 446–452.

S.J. Miller, et al., Application of Ring Closing Methathesis to the Synthesis of Regidified Amino Acids & Peptides, J. Am. Chem. Soc. 1996, 118. 9606–9614.

C. Grünwald, et al., Five Coordinate 16–Electron Carbene—Organomettalics, 1996, 15, 1960–1962.

D.M. Lynn, et al., Living Ring–Opening Metathesis Polymerization, J. Am. Chem. Soc., 1996,118, 784–790.

B. Mohr, et al., Synthesis of Water–Soluble, Aliphatic Phosphines and Organomettalics, 1996, 15, 4317–4325.

P. Schwab, et al., Sythesis and Applications of J. Am. Chem. Soc. 1996, 118, 100–110.

*Primary Examiner*—Porfirio Nazario-Gonzalez
*Attorney, Agent, or Firm*—Luther A.R. Hall; Jacob M. Levine

[57] ABSTRACT

A process for the preparation of a metal carbene, in which a metal salt is first reacted in the presence of a base and a secondary or tertiary alcohol with a tertiary phosphine or phosphite or a ditertiary diphosphine or diphosphite and then reacted in the presence of an acid with an alkyne and, if desired, an alkene.

9 Claims, No Drawings

PROCESS FOR THE PREPARATION OF CATALYSTS

The present invention relates to a process for the preparation of ruthenium and osmium carbene catalysts.

The thermal metathesis polymerisation of strained cycloolefins, which has recently acquired great importance, requires catalysts that are mainly compounds of transition metals. Whereas, initially, systems consisting of catalyst and co-catalyst were normally used (see, for example, U.S. Pat. No. 4,060,468 and WO 93/13171), one-component catalysts are also known [Thoi, H. H., Ivin, K. J., Rooney, J. J., J. Mol. Catal. 15:245–270 (1982)]. More recently, so-called "metal carbenes", ruthenium and osmium compounds having a =CR'R" group bonded to the metal atoms, have been found to be especially interesting compounds for that application [WO 93/20111; Kanaoka, S., Grubbs, R. H., Macromolecules 28:4707–4713 (1995); Fraser, C., Hillmyer, M., Gutierrez, E., Grubbs, R. H., Polym. Prepr. 36:237–238 (1995); Schwab, P., France, M. B., Ziller, J. W., Grubbs, R. H., Angew. Chem. 107:2179–2181 (1995)].

That type of compound is also suitable for catalysing ring-closure in dienes (WO 96/04289).

Schwab et al. [Schwab, P., Grubbs, R. H., Ziller, J. W., J. Am. Chem. Soc. 118:100–110 (1996); Schwab, P., France, M. B., Ziller, J. W., Grubbs, R. H., Angew. Chem. Int. Ed. Engl. 34:2039–2041 (1995)] describe the synthesis of ruthenium carbenes using diazoalkanes. In WO 96/04289, the synthesis of vinyl-ruthenium carbenes using cyclopropenes is disclosed. Both the diazoalkanes and the cyclopropenes are thermally unstable and are not available commercially. It is therefore necessary to prepare them first in a complicated process shortly before the synthesis. Furthermore, diazoalkanes are generally toxic, and are difficult to handle owing to their explosive nature.

Grünwald et al. [Grünwald, C., Gevert, O., Wolf, J., Gonzàlez-Herrero, P., Werner, H., Organometallics 15:1960–1962 (1996)] describe the preparation of ruthenium carbene catalysts using alkynes, a 100% excess of phosphines and $H_2$ pressure.

Surprisingly, it has now been found that ruthenium and osmium carbenes can be synthesised extremely well using readily obtainable Ru or Os salts and an alkyne and, if desired, an alkene. In the process of the invention, the use of $H_2$ is superfluous. The process can be carried out under normal pressure and in the presence of water. In addition, no thermally unstable cyclopropene or diazoalkane compounds are used. Only commercially obtainable, low-priced reagents are used. In comparison with the method described by Grünwald et al. [Grünwald, C., Gevert, O., Wolf, J., Gonzàlez-Herrero, P., Werner, H., Organometallics 15:1969–1962 (1996)], the reaction proceeds more rapidly, less phosphine/Ru is used and the yield is altogether higher.

The compounds prepared by the process of the invention are extraordinarily suitable as catalysts in the polymerisation of cyclic olefins and in the ring-closure of dienes.

The invention relates firstly to a process for the preparation of a compound of the formula:

$$X^{01}\diagdown_{X^{02}\diagup}\!\!\!\overset{T^1}{\underset{T^2}{|}}Me\!=\!\!CHCH_2T^3, \quad (I)$$

wherein

Me is ruthenium or osmium;

$X^{01}$ and $X^{02}$ are each independently of the other halogen;

$T^1$ and $T^2$ are each independently of the other a tertiary phosphine or phosphite, or $T^1$ and $T^2$ together are a ditertiary diphosphine or diphosphite; and $T^3$ is hydrogen, $C_1$–$C_{20}$alkyl, $C_3$–$C_8$cycloalkyl, $C_3$–$C_7$heterocycloalkyl having one or two hetero atoms selected from the group oxygen, sulfur and nitrogen, $C_6$–$C_{14}$aryl, or $C_4$–$C_{15}$heteroaryl having from one to three hetero atoms selected from the group oxygen, sulfur and nitrogen, wherein alkyl, cycloalkyl, heterocycloalkyl, aryl and heteroaryl are unsubstituted or substituted by $C_1$–$C_4$alkyl, $C_1$–$C_4$haloalkyl, $C_1$–$C_4$alkoxy, $C_6$–$C_{10}$aryl, $C_6$–$C_{10}$aryloxy, —$NO_2$ or by halogen;

in which a metal salt of the formula:

$$X^{01}\diagdown_{X^{02}\diagup}\!\!\!\overset{L^1_n}{\underset{L^4_n}{|}}\!\!\!Me\!\diagup\!\!\!\overset{L^2_n}{\underset{L^3_n,}{|}} \quad (II)$$

wherein

Me, $X^{01}$ and $X^{02}$ are as defined above, $L^1$, $L^2$, $L^3$ and $L^4$ are each independently of the others a neutral ligand, and n is 0 or 1;

is first reacted in the presence of a base and a secondary or tertiary alcohol with a tertiary phosphine or phosphite or a ditertiary diphosphine or diphosphite and then reacted in the presence of an acid with an alkyne of the formula:

$$HC\!\equiv\!C\!-\!T^2, \quad (III)$$

wherein $T^3$ is as defined above.

The present invention further relates to a process for the preparation of a compound of the formula:

$$X^{01}\diagdown_{X^{02}\diagup}\!\!\!\overset{T^1}{\underset{T^2}{|}}Me\!=\!\!CHT^3, \quad (Ia)$$

wherein

Me is ruthenium or osmium;

$X^{01}$ and $X^{02}$ are each independently of the other halogen;

$T^1$ and $T^2$ are each independently of the other a tertiary phosphine or phosphite, or $T^1$ and $T^2$ together are a ditertiary diphosphine or diphosphite; and $T^3$ is hydrogen, $C_1$–$C_{20}$alkyl, $C_3$–$C_8$cycloalkyl, $C_3$–$C_7$heterocycloalkyl having one or two hetero atoms selected from the group oxygen, sulfur and nitrogen, $C_6$–$C_{14}$aryl, or $C_4$–$C_{15}$heteroaryl having from one to three hetero atoms selected from the group oxygen, sulfur and nitrogen, wherein alkyl, cycloalkyl, heterocycloalkyl, aryl and heteroaryl are unsubstituted or substituted by $C_1$–$C_4$alkyl, $C_1$–$C_4$haloalkyl, $C_1$–$C_4$alkoxy, $C_6$–$C_{10}$aryl, $C_6$–$C_{10}$aryloxy, —$NO_2$ or by halogen;

in which a compound of the formula:

$$X^{01}\diagdown_{X^{02}\diagup}\!\!\!\overset{T^1}{\underset{T^2}{|}}Me\!=\!\!CHCH_2T^3, \quad (I)$$

wherein

Me, $T^1$, $T^2$, $T^3$, $X^{01}$ and $X^{02}$ are as defined above, is reacted with an alkene of the formula:

$$H_2C{=}\overset{H}{C}{-}T^3, \qquad (IIIa)$$

wherein $T^3$ is as defined above.

Me in formulae I and Ia is preferably ruthenium.

According to the invention, halogen is F, Cl, Br or I. $X^{01}$ and $X^{02}$ in formulae I and Ia are preferably F, Cl or Br, especially Cl or Br, and more especially are each Cl.

The tertiary phosphines and phosphites and ditertiary diphosphines and diphosphites contain preferably from 3 to 40, especially from 3 to 30 and more especially from 3 to 24, carbon atoms.

The tertiary phosphines or phosphites and the ditertiary diphosphines or diphosphites preferably correspond to the formulae:

$$PR^1R^2R^3, \qquad (IV)$$

$$R^1R^2P{-}Z{-}PR^1R^2, \qquad (IVa)$$

$$P(OR^1)(OR^2)OR^3 \qquad (IVb)$$

$$R^1OP(OR^2){-}Z{-}(OR^2)POR^1, \qquad (IVc)$$

wherein $R^1$, $R^2$ and $R^3$ are each independently of the others $C_1$–$C_{20}$alkyl, $C_4$–$C_{12}$cycloalkyl, $C_2$–$C_{11}$heterocycloalkyl, $C_6$–$C_{16}$aryl, $C_2$–$C_{15}$heteroaryl or $C_7$–$C_{16}$aralkyl, wherein alkyl, cycloalkyl, heterocycloalkyl, aryl, heteroaryl and aralkyl are unsubstituted or substituted by a substituent selected from the group consisting of $C_1$–$C_6$alkyl, $C_1$–$C_6$alkoxy, $C_1$–$C_6$haloalkyl, $C_6$–$C_{16}$aryl, $-NO_2$, $SO_3^-$, ammonium and halogen; the radicals $R^1$ and $R^2$ together are tetra- or penta-methylene which is unsubstituted or substituted by $C_1$–$C_6$alkyl, $C_1$–$C_6$haloalkyl, $-NO_2$ or by $C_1$–$C_6$alkoxy, or are tetra- or penta-methylene which is unsubstituted or substituted by $C_1$–$C_6$alkyl, $C_1$–$C_6$haloalkyl, $-NO_2$ or by $C_1$–$C_6$alkoxy and condensed with one or two 1,2-phenylene(s), and $R^3$ is as defined above; and Z is linear or branched, unsubstituted or $C_1$–$C_4$alkoxy-substituted $C_2$–$C_{12}$alkylene; unsubstituted or $C_1$–$C_4$alkyl- or $C_1$–$C_4$alkoxy-substituted 1,2- or 1,3-cycloalkylene having from 4 to 8 carbon atoms; unsubstituted or $C_1$–$C_4$alkyl- or $C_1$–$C_4$alkoxy-substituted 1,2- or 1,3-heterocycloalkylene having 5 or 6 ring members and one hetero atom from the group O atom and N atom, unsubstituted or $C_1$–$C_4$alkyl- or $C_1$–$C_4$alkoxy-substituted 1,2-phenylene; 1-methylene-phen-2-yl; 1,2-dimethylenebenzene or unsubstituted or $C_1$–$C_4$alkyl- or $C_1$–$C_4$alkoxy-substituted 2,2'-biphenylene.

The neutral ligands in the definition of $L^1$, $L^2$, $L^3$ and $L^4$ are preferably $C_2$–$C_{12}$alkene, $C_3$–$C_{12}$ cycloalkene, $C_6$–$C_{14}$arene, $C_4$–$C_{12}$heteroarene, an ether, a phosphine, a phosphite, a nitrile, an isonitrile, a dialkyl sulfoxide, $H_2O$ or an amine.

Examples of alkyl are methyl, ethyl and the isomers of propyl, butyl, pentyl, hexyl, heptyl, octyl, nonyl, decyl, undecyl and dodecyl. An example of aryl-substituted alkyl is benzyl. Examples of alkoxy are methoxy, ethoxy and the isomers of propoxy and butoxy. Examples of alkylene are methylene, ethylene and the isomers of propylene, butylene, pentylene, hexylene, heptylene, octylene, nonylene, decylene, undecylene and dodecylene.

Examples of alkene are ethene, propene, butene, butadiene, pentene and the isomers of pentadiene, hexadiene, heptadiene, octadiene, nonadiene, decadiene and hexatriene and the isomers of heptatriene, octatriene, nonatriene and decatriene.

Some examples of cycloalkyl are cyclobutyl, cycloheptyl, cyclooctyl and especially cyclopentyl and cyclohexyl. Examples of substituted cycloalkyl are methyl-, dimethyl-, trimethyl-, methoxy-, dimethoxy-, trimethoxy-, trifluoromethyl-, bistrifluoromethyl- and tristrifluoromethyl-cyclopentyl and -cyclohexyl. Examples of cycloalkylene are 1,2- and 1,3-cyclopentylene and 1,2- and 1,3-cyclohexylene.

Examples of cycloalkene are cyclopentene, cyclohexene, cycloheptene, cyclooctene, cyclododecene, cyclohexadiene, cycloheptadiene and the isomers of cyclooctadiene and cyclooctatetraene and bicyclo[2.2.1]hepta-2,5-diene.

Some examples of heterocycloalkyl are tetrahydrofuranyl, pyrrolidinyl, piperazinyl and tetrahydrothiophenyl. Examples of heterocycloalkylene are 1,2- and 1,3-pyrrolidine, 1,2- and 1,3-piperidine and also 1,2- and 1,3-tetrahydrofuran.

Examples of aryl are phenyl and naphthyl. Examples of aryloxy are phenyloxy and naphthyloxy. Examples of substituted aryl are methyl-, dimethyl-, trimethyl-, methoxy-, dimethoxy-, trimethoxy-, trifluoromethyl-, bistrifluoromethyl- and tristrifluoromethyl-phenyl. An example of aralkyl is benzyl. Examples of substituted aralkyl are methyl-, dimethyl-, trimethyl-, methoxy-, dimethoxy-, trimethoxy-, trifluoromethyl-, bistrifluoromethyl- and tristrifluoromethyl-benzyl. Some examples of heteroaryl are furanyl, thiophenyl, pyrrolyl, pyridinyl and pyrimidinyl.

The arenes and heteroarenes are, for example, benzene, cumene, biphenyl, naphthalene, anthracene, acenaphthene, fluorene, phenanthrene, pyrene, chrysene, fluoranthrene, furan, thiophene, pyrrole, pyridine, γ-pyran, γ-thiopyran, pyrimidine, pyrazine, indole, coumarone, thionaphthene, carbazole, dibenzofuran, dibenzothiophene, pyrazole, imidazole, benzimidazole, oxazole, thiazole, isoxazole, isothiazole, quinoline, isoquinoline, acridine, chromene, phenazine, phenoxazine, phenothiazine, triazines, thianthrene or purine.

The nitriles and isonitriles within the scope of the present invention are compounds of the formula $R^9$—CN or $R^9$—NC, wherein $R^9$ is $C_1$–$C_{12}$alkyl, $C_3$–$C_8$cycloalkyl, $C_3$–$C_7$heterocycloalkyl having one or two hetero atoms selected from the group oxygen, sulfur and nitrogen, $C_6$–$C_{14}$aryl, or $C_4$–$C_{15}$heteroaryl having from one to three hetero atoms selected from the group oxygen, sulfur and nitrogen, wherein alkyl, cycloalkyl, heterocycloalkyl, aryl and heteroaryl are unsubstituted or substituted by $C_1$–$C_4$alkyl, $C_1$–$C_4$haloalkyl, $C_1$–$C_4$alkoxy, $C_6$–$C_{10}$aryl, $C_6$–$C_{10}$aryloxy, $-NO_2$ or by halogen.

Examples of dialkyl sulfoxide are dimethyl sulfoxide, diethyl sulfoxide, tetramethylene sulfoxide and pentamethylene sulfoxide.

Examples of ethers are dibutyl ether, tetrahydrofuran, dioxane, ethylene glycol monomethyl or dimethyl ether, ethylene glycol monoethyl or diethyl ether, diethylene glycol diethyl ether and triethylene glycol dimethyl ether.

Within the scope of the present invention, amines correspond to the formula $R^{10}R^{11}R^{12}N$ and ammonium corresponds to the formula $R^{10}R^{11}R^{12}N^+$, wherein $R^{10}$, $R^{11}$ and $R^{12}$ are each independently of the others hydrogen, $C_1$–$C_{18}$alkyl, unsubstituted or $C_1$–$C_4$alkyl- or $C_1$–$C_4$alkoxy-substituted $C_5$- or $C_6$-cycloalkyl, or unsubstituted or $C_1$–$C_4$alkyl- or $C_1$–$C_4$alkoxy-substituted $C_6$–$C_{18}$aryl or $C_7$–$C_{12}$aralkyl; or $R^{10}$ and $R^{11}$ together are tetramethylene, pentamethylene, 3-oxa-1,5-pentylene or $-[CH_2]_2NH$ $[CH_2]_2$— or —$[CH_2]_2N(C_1$–$C_4$alkyl)—$[CH_2]_2$—, and $R^{12}$ independently has the definition of $R^{10}$. The alkyl contains preferably from 1 to 12 and especially from 1 to 6 carbon atoms. The aryl contains preferably from 6 to 12 carbon atoms and the aralkyl contains preferably from 7 to 9 carbon atoms. Examples of amines are methyl-, dimethyl-, trimethyl-, ethyl-, diethyl-, triethyl-, methyl-ethyl-, dimethyl-ethyl-, n-propyl-, di-n-propyl-, tri-n-butyl-, cyclohexyl-, phenyl- and benzyl-amine, and also pyrrolidine, N-methylpyrrolidine, piperidine, piperazine, morpholine and N-methylmorpholine.

The radicals $R^1$, $R^2$ and $R^3$ are preferably identical radicals. Furthermore, radicals $R^1$, $R^2$ and $R^3$ that are sterically demanding, for example cyclic or branched, especially α,α-di-branched and more especially α-branched, alkyl groups, are most especially preferred.

When $R^1$, $R^2$ and $R^3$ are substituted, the substituents are preferably $C_1$–$C_4$alkyl, $C_1$–$C_4$haloalkyl, $C_1$–$C_4$alkoxy, $SO_3^-$ or ammonium. Halogen is preferably Cl and especially F. Examples of preferred substituents are methyl, methoxy, ethyl, ethoxy and trifluoromethyl. $R^1$, $R^2$ and $R^3$ may be substituted, for example, by from 1 to 3 substituents.

$R^1$, $R^2$ and $R^3$ as alkyl may be linear or branched and contain preferably from 1 to 12, especially from 1 to 8 and more especially from 1 to 6, carbon atoms. Preferred examples are methyl, ethyl, n- and iso-propyl, n-, iso-, sec- and tert-butyl, 1-, 2- or 3-pentyl and 1-, 2-, 3- or 4-hexyl. Sterically demanding branched alkyl groups are especially preferred.

When $R^1$, $R^2$ and $R^3$ are cycloalkyl, they are preferably $C_5$–$C_8$cycloalkyl and especially $C_5$- or $C_6$-cycloalkyl.

When $R^1$, $R^2$ and $R^3$ are aryl, they are preferably $C_6$–$C_{12}$aryl and especially phenyl or naphthyl.

When $R^1$, $R^2$ and $R^3$ are aralkyl, they are preferably $C_7$–$C_{13}$aralkyl, the alkylene group in the aralkyl preferably being methylene. Aralkyl is especially benzyl.

Examples of unsubstituted or substituted and, as the case may be, condensed tetra- and penta-methylene bonded to the P atom are:

Other suitable phosphines are cycloaliphates having from 6 to 8 ring carbon atoms and bridged by a =$PR^4$ group, for example wherein $R^4$ is $C_1$–$C_6$alkyl, cyclohexyl, benzyl, or phenyl that is unsubstituted or substituted by one or two $C_1$–$C_4$alkyl substituents.

Z as linear or branched alkylene is preferably 1,2-alkylene or 1,3-alkylene having preferably from 2 to 6 carbon atoms, for example ethylene, 1,2-propylene or 1,2-butylene.

Preference is given to tertiary phosphines of formula IV wherein $R^1$, $R^2$ and $R^3$ are each independently of the others $C_1$–$C_{20}$alkyl, $C_4$–$C_{12}$cycloalkyl or $C_6$–$C_{16}$aryl, wherein alkyl, cycloalkyl and aryl are unsubstituted or substituted by a substituent selected from the group consisting of $C_1$–$C_6$alkyl, $C_1$–$C_6$alkoxy, $C_1$–$C_6$haloalkyl, $C_6$–$C_{16}$aryl, —$NO_2$, $SO_3^-$, ammonium and halogen. Especially preferred examples of tertiary phosphines of formula IV are $(C_6H_5)_2$(iso-$C_3H_7$)P, $(C_6H_5)$(iso-$C_3H_7$)$_2$P, $(C_6H_5)_2(C_6H11)$P, $(C_6H_5)_3$P, $(C_6H_5CH_2)_3$P, $(C_5H_9)_3$P, (2,3-di-tert-$C_4H_9$—$C_6H_3)_3$P, (2,6-di-tert-$C_4H_9$—$C_6H_3)_3$P, (3-$CH_3$-6-tert-$C_4H_9$—$C_6H_3)_3$P, $(C_6H_{11})_3$P, (2-$CH_3$-6-tert-$C_4H_9$—$C_6H_3)_3$P, (4-tert-$C_4H_9$—$C_6H_4)_3$P, (3-tert-$C_4H_9$—$C_6H_4)_3$P, (2-tert-$C_4H_9$—$C_6H_4)_3$P, (4-iso-$C_4H_9$—$C_6H_4)_3$P, $(CH_3)_3$P, $(C_2H_5)_3$P, (n-$C_3H_7)_3$P, (iso-$C_3H_7)_3$P, (n-$C_4H_9)_3$P, (3-iso-$C_4H_9$—$C_6H_4)_3$P, (2-iso-$C_4H_9$—$C_6H_4)_3$P, (4-n-$C_4H_9$—$C_6H_4)_3$P, (3-n-$C_4H_9$—$C_6H_4)_3$P, (sec-$C_4H_9)_3$P, (2-$CH_3$—$C_6H_4)_3$P, (3-$CH_3$—$C_6H_4)_3$P, (4-$CH_3$—$C_6H_4)_3$P, (2,4-di-$CH_3$—$C_6H_3$)$_3$P, (2,6-di-$CH_3$—$C_6H_3)_3$P, (2-$C_2H_5$—$C_6H_4)_3$P, (3-$C_2H_5$—$C_6H_4)_3$P, (4-$C_2H_5$—$C_6H_4)_3$P, (2-n-$C_3H_7$—$C_6H_4)_3$P, (3-n-$C_3H_7$—$C_6H_4)_3$P, (4-n-$C_3H_7$—$C_6H_4)_3$P, (2-iso-$C_3H_7$—$C_6H_4)_3$P, (3-iso-$C_3H_7$—$C_6H_4)_3$P, (4-iso-$C_3H_7$—$C_6H_4)_3$P, $(C_6H_5)(C_6H_{11})_2$P, (2-n-$C_4H_9$—$C_6H_4)_3$P, $(C_6H_5)$(sec-$C_4H_9)_2$P, $(C_6H_{11})[C(C_2H_4)_2(N(CH_3)_3Cl)]$P, $(C_6H_{11})_2[CH_2CH_2N(CH_3)_3Cl]$P, $(C_6H_{11})_2[CH_2CH_2SO_3Na]$P and (2,4-di-tert-$C_4H_9$—$C_6H_3)_3$P.

Examples of phosphites are $(CH_3O)_3$P, $(C_2H_5O)_3$P, (n-$C_3H_7O)_3$P, (iso-$C_3H_7O)_3$P, (n-$C_4H_9O)_3$P, (2,6-di-tert-$C_4H_9$—$C_6H_3O)_3$P, (2,3-di-tert-$C_4H_9$—$C_6H_3O)_3$P, (2,4-di-tert-$C_4H_9$—$C_6H_3O)_3$P, (iso-$C_4H_9O)_3$P, (4-$CH_3$—$C_6H_4O)_3$P, (tert-$C_4H_9O)_3$P, $(C_6H_5O)_3$P, (2,4-di-$CH_3$—$C_6H_3O)_3$P, (2,6-di-$CH_3$—$C_6H_3O)_3$P, (2-$C_2H_5$—$C_6H_4O)_3$P, (3-$CH_3$-6-tert-$C_4H_9$—$C_6H_3O)_3$P, (3-$CH_3$-6-tert-$C_4H_9$—$C_6H_3O)_3$P, (3-$C_2H_5$—$C_6H_4O)_3$P, (2-$CH_3$-6-tert-$C_4H_9$—$C_6H_3O)_3$P, (4-$C_2H_5$—$C_6H_4O)_3$P, (2-n-$C_3H_7$—$C_6H_4O)_3$P, (3-n-$C_3H_7$—$C_6H_4O)_3$P, (4-n-$C_3H_7$—$C_6H_4O)_3$P, (3-n-$C_4H_9$—$C_6H_4O)_3$P, (2-n-$C_4H_9$—$C_6H_4O)_3$P, (4-n-$C_4H_9$—$C_6H_4O)_3$P, (2-iso-$C_3H_7$—$C_6H_4O)_3$P, (3-iso-$C_3H_7$—$C_6H_4O)_3$P, (4-iso-$C_4H_9$—$C_6H_4O)_3$P, (2-$CH_3$—$C_6H_4O)_3$P, (3-$CH_3$—$C_6H_4O)_3$P, (3-iso-$C_3H_7$—$C_6H_4O)_3$P, (4-iso-$C_3H_7$—$C_6H_4O)_3$P, (2-iso-$C_4H_9$—$C_6H_4O)_3$P, (2-tert-$C_4H_9$—$C_6H_4O)_3$P, (3-tert-$C_4H_9$—$C_6H_4O)_3$P and (4-tert-$C_4H_9$—$C_6H_4O)_3$P.

$T^3$ as alkyl may contain preferably from 1 to 12 and especially from 1 to 8 carbon atoms. $T^3$ is especially linear $C_1$–$C_8$alkyl.

$T^3$ as cycloalkyl may contain preferably from 5 to 8 carbon atoms. Cyclopentyl and cyclohexyl are especially preferred.

$T^3$ as heterocycloalkyl may contain preferably 4 or 5 carbon atoms and preferably one hetero atom selected from the group oxygen, sulfur and nitrogen.

$T^3$ as aryl may contain preferably from 6 to 10 carbon atoms. Preferred examples are naphthyl and, especially, phenyl and substituted phenyl.

$T^3$ as heteroaryl may contain preferably 4 or 5 carbon atoms and one or two hetero atom(s) selected from the group oxygen, sulfur and nitrogen.

Preferred substituents of $T^3$ are methyl, ethyl, methoxy, ethoxy, trichloromethyl, trifluoromethyl, phenyl, phenyloxy, F, Cl, isopropyl, tert-butyl and OH.

In a preferred embodiment, $T^3$ is hydrogen, $C_1$–$C_9$alkyl, cyclopentyl, cyclohexyl, phenyl or naphthyl, which are unsubstituted or substituted by $C_1$–$C_4$alkyl, $C_1$–$C_4$alkoxy, $C_1$–$C_4$haloalkyl, phenyl, F or by Cl. For example, $T^3$ is preferably benzyl.

A preferred sub-group of the compounds of formulae I and Ia is formed by those of the formulae:

$$\begin{array}{c} P(R^5)_3 \\ Cl \diagdown | \\ \phantom{Cl}Me = CHCH_2T^3, \\ Cl \diagup | \\ P(R^5)_3 \end{array} \quad (Ib)$$

$$\begin{array}{c} P(R^5)_3 \\ Cl \diagdown | \\ \phantom{Cl}Me = CHT^3, \\ Cl \diagup | \\ P(R^5)_3 \end{array} \quad (Ic)$$

wherein

Me is Ru or Os, $R^5$ is α-branched $C_3$–$C_8$alkyl, or $C_5$–$C_8$cycloalkyl which is unsubstituted or substituted by $C_1$–$C_4$alkyl, $C_1$–$C_4$haloalkyl, $C_1$–$C_4$alkoxy, halogen or by —$NO_2$, or $C_6$–$C_{10}$aryl which is unsubstituted or substituted by $C_1$–$C_4$alkyl, $C_1$–$C_4$haloalkyl, $C_1$–$C_4$alkoxy, halogen or by —$NO_2$, and $T^3$ is hydrogen, $C_1$–$C_6$alkyl, or $C_5$–$C_8$cycloalkyl which is unsubstituted or substituted by $C_1$–$C_4$alkyl, $C_1$–$C_4$haloalkyl, $C_1$–$C_4$alkoxy, halogen or by —$NO_2$, or $C_6$–$C_{10}$aryl which is unsubstituted or substituted by $C_1$–$C_4$alkyl, $C_1$–$C_4$haloalkyl, $C_1$–$C_4$alkoxy, halogen or by —$NO_2$.

Some specific and preferred examples of compounds of formulae I and Ia are [Me is Os and preferably Ru]:
$Cl_2[P(C_6H_{11})_2$—$CH_2CH_2$—$P(C_6H_{11})_2]Me$=$CH$—$C_6H_5$,
$Cl_2[P(C_6H_{11})_3]_2Me$=$CH$—$C_6H_4$—$CH(CH_3)_2$,
$Cl_2[P(iso-C_3H_7)_3]_2Me$=$CH$—$[C_6H_4(tert-C_4H_9)]$, $Cl_2[P(C_6H_{11})_3]_2Me$=$CH_2$, $Cl_2[P(C_5H_9)_3]_2Me$=$CH_2$,
$Cl_2[P(C_6H_{11})_3]_2Me$=$CH$—$[C_6H_4(tert-C_4H_9)]$, $Cl_2[P(C_5H_9)_3]_2Me$=$CH$—$CH_3$,
$Cl_2[P(C_6H_{11})_3]_2Me$=$CHCH_3$, $Cl_2[P(C_6H_5)_3]_2Me$=$CH$—$C_6H_5$, $F_2[P(C_5H_9)_3]_2Me$=$CH$—$C_6H_5$,
$Br_2[P(C_6H_{11})_3]_2Me$=$CH$—$C_6H_2$—$(CH_3)_3$, $Br_2[P(C_5H_9)_3]_2Me$=$CH$—$C_6H_5$, $Cl_2[P(C_5H_9)_3]_2Me$=$CH$—$C_5H_9$,
$Br_2[P(C_5H_9)_3]_2Me$=$CH(C_6H_4$—$OC_2H_5)$, $Cl_2[P(C_5H_9)_3]_2Me$=$CH$—$C_6H_5$, $F_2[P(C_6H_{11})_3]_2Me$=$CH$—$C_6H_5$,
$Cl_2[P(iso-C_3H_7)_3]_2Me$=$CH$—$[C_6H_4(CH_3)]$, $Cl_2[P(C_5H_9)_3]_2Me$=$CH$—$C_6H_{11}$,
$Cl_2[P(C_5H_9)_3]_2Me$=$CH$—$C_6H_{11}$, $Cl_2[P(C_6H_2$—$(CH_3)_3)_3]_2Me$=$CH$—$C_6H_5$, $Br_2[P(C_6H_{11})_3]_2Me$=$CH$—$C_6H_5$,
$Cl_2[P(C_6H_{11})_3]_2Me$=$CH$—$C_6H_5$, $Br_2[P(C_5H_4$—$(CH_3)_2)_3]_2Me$=$CH$—$C_6H_5$,
$Br_2[P(C_5H_9)_3]_2Me$=$CH$-$iso$-$C_3H_7$, $Cl_2[P(iso-C_3H_7)_3]_2Me$=$CH$—$C_6H_5$,
$Br_2[P(C_6H_{11})_3]_2Me$=$CH(C_6H_4$—$NO_2)$, $Cl_2[P(C_6H_{11})_3]_2Me$=$CH$-$tert$-$C_4H_9$,
$Cl_2[P(C_5H_9)_3]_2Me$=$CH$-$n$-$C_4H_9$, $Cl_2[P(C_6H_4$—$CH_3)_3]_2Me$=$CH$—$C_6H_5$,
$Cl_2[P(C_6H_{11})_3]_2Me$=$CH$-$n$-$C_4H_9$, $Cl_2[P(C_6H_{11})_3]_2Me$=$CH$—$C_{10}H_9$, $Cl_2[P(C_6H_{11})_3]_2Me$=$CH(C_6H_4$—$Cl)$,
$Cl_2[P(C_5H_9)_3]_2Me$=$CH(C_6H_4$—$Br)$, $Cl_2[P(C_6H_{11})_3]_2Me$=$CH$—$C_6H_4$—$OCH_3$,
$Cl_2[P(C_5H_9)_3]_2Me$=$CH$—$C_6H_3$—$(CH_3)_2$, $F_2[P(C_5H_9)_3]_2Me$=$CH[C_6H_3$—$(CH_3)_2]$,
$Br_2[P(C_5H_9)_3]_2Me$=$CH$—$CH_2C_6H_5$, $Cl_2[P(C_6H_{11})_3]_2Me$=$CH(C_6H_4$—$CH_3)$,
$Cl_2[P(sec-C_4H_9)_3]_2Me$=$CH$—$C_6H_5$, $BrCl[P(C_6H_{11})_3]_2Me$=$CH$—$C_6H_5$,
$BrCl[P(iso-C_3H_7)_3]_2Me$=$CH$—$C_6H_5$, $BrCl[P(C_6H_{11})_3]_2Me$=$CH$—$CH_2C_6H_5$,
$Cl_2[P(C_6H_{11})_2(C(CH_2CH_2)_2N(CH_3)_3Cl)]_2Me$=$CH$—$C_6H_5$,
$Cl_2[P(C_6H_{11})_2(CH_2CH_2SO_3Na)]_2Me$=$CH$—$C_6H_5$, $Cl_2[P(C_6H_{11})_2(CH_2CH_2N(CH_3)_3Cl)]_2Me$=$CH$—$C_6H_5$ and $BrCl[P(iso-C_3H_7)_3]_2Me$=$CH$—$CH_2C_6H_5$.

$L^1$, $L^2$, $L^3$ and $L^4$ are preferably selected from the group consisting of $H_2O$, $C_2$–$C_{12}$alkene, $C_3$–$C_{12}$cycloalkene, dimethyl sulfoxide, tertiary phosphine and tertiary amine. Special preference is given to $H_2O$ and cycloalkenes such as norbornadiene and cyclooctadiene.

Within the scope of the present invention, any base (proton acceptor) and any acid (proton donor) is suitable. Preferred bases are those having a greater basicity than water. Examples are tertiary amines, metal hydroxides, metal alcoholates and metal phenolates. Preferred bases are triethylamine, 1,8-diazabicyclo[5.4.0]undec-7-ene, KOH, NaOH, KO-tert-butyl and NaO-methyl, especially triethylamine and 1,8-diazabicyclo[5.4.0]undec-7-ene.

Preferred acids are hydrohalic acids. Examples are selected from the group consisting of HF, HCl, HBr and HI, special preference being given to HCl and HBr.

The secondary and tertiary alcohols are advantageously compounds of the formula $HC(R^6)(R^7)OH$ or $R^6C(R^7)(R^8)OH$, wherein $R^6$, $R^7$ and $R^8$ are each independently of the others $C_1$–$C_{20}$alkyl, or $C_4$–$C_{12}$cycloalkyl which is unsubstituted or substituted by $C_1$–$C_6$alkyl, $C_1$–$C_6$haloalkyl, —$NO_2$ or by $C_1$–$C_6$alkoxy, or $C_6$–$C_{16}$aryl which is unsubstituted or substituted by $C_1$–$C_6$alkyl, $C_1$–$C_6$haloalkyl, —$NO_2$ or by $C_1$–$C_6$alkoxy, or $C_7$–$C_{16}$aralkyl which is unsubstituted or substituted by $C_1$–$C_6$alkyl, $C_1$–$C_6$haloalkyl, —$NO_2$ or by $C_1$–$C_6$alkoxy; or the radicals $R^6$ and $R^7$ together are tetra- or penta-methylene which is unsubstituted or substituted by $C_1$–$C_6$alkyl, $C_1$–$C_6$haloalkyl, —$NO_2$ or by $C_1$–$C_6$alkoxy, or tetra- or penta-methylene which is unsubstituted or substituted by $C_1$–$C_6$alkyl, $C_1$–$C_6$haloalkyl, —$NO_2$ or by $C_1$–$C_6$alkoxy and condensed with one or two 1,2-phenylene(s), and $R^8$ is as defined above.

$R^6$, $R^7$ and $R^8$ are preferably each independently of the others $C_1$–$C_{20}$alkyl, or $C_4$–$C_{12}$cycloalkyl which is unsubstituted or substituted by $C_1$–$C_6$alkyl, $C_1$–$C_6$haloalkyl, —$NO_2$ or by $C_1$–$C_6$ alkoxy. $R^6$, $R^7$ and $R^8$ are especially each independently of the others $C_1$–$C_{10}$alkyl or $C_4$–$C_{12}$cycloalkyl. Special preference is given to methyl, ethyl, propyl, isopropyl, butyl, isobutyl and sec-butyl.

The process of the invention is advantageously carried out by suspending the metal salt, base and phosphine or phosphite in the secondary or tertiary alcohol. By heating to a temperature in the range of from 0° C. to 150° C., preferably from 60° C. to 100° C., especially from 80° C. to 90° C., the temperature chosen depending especially on the boiling point of the alcohol used, the suspension turns into a solution.

The acid and alkyne are added to the solution, the order in which this is done being of no consequence. It has been found advantageous to add the acid first and only then to add the alkyne. A favourable reaction temperature for this step is in the range of from –150° C. to 150° C., preferably from –100° C. to 60° C. and especially from –80° C. to room temperature.

The process of the invention is especially carried out by
  (a) suspending the metal salt, base and phosphine or phosphite in the secondary or tertiary alcohol,
  (b) heating the suspension to a temperature in the range of the boiling point of the alcohol used,
  (c) adding the acid and alkyne to the resulting solution and
  (d) reacting the reaction mixture at a temperature in the range of from –150° C. to 150° C.

The reaction of the compounds of formula I is advantageously effected at a temperature in the range of from 0° C. to 100° C., preferably from room temperature to 50° C.

All the reaction steps are usually carried out under normal pressure, it having been found advantageous especially for the preparation of the compounds of formula I to carry out the reaction steps in an inert atmosphere, preferably in a nitrogen or argon atmosphere.

The mass ratio of phosphine or phosphite, base, acid or alkyne to the metal salt is generally in the range of from 2:1 to 100:1, the ratio 2:1 being preferred.

The mass ratio of alkene to compound of formula I is generally in the range of from 1:1 to 100:1, preferably from 1:1 to 10:1, the ratio 5:1 being especially preferred.

The resulting compounds of formulae I and Ia are worked up by known methods as described, for example, in WO 96/04289, Schwab et al. [Schwab, P., Grubbs, R. H., Ziller, J. W., J. Am. Chem. Soc. 118:100–110 (1996)] and Grünwald et al. [Grünwald, C., Gevert, O., Wolf, J., Gonzàlez-Herrero, P., Werner, H., Organometallics 15:1960–1962 (1996)].

The cyclic olefins that can be polymerised using the catalysts prepared in accordance with the invention are known and are described, for example, in WO 96/24629 (FM/6-20336/A). They are preferably monocyclic or polycyclic condensed and/or bridged and/or linked ring systems, for example having from two to four rings, which are unsubstituted or substituted and may contain hetero atoms, for example an O, S, N or Si atom, in one or more rings and/or may contain condensed aromatic or heteroaromatic rings, for example o-phenylene, o-naphthylene, o-pyridinylene or o-pyrimidinylene. The cycloolefins are preferably norbornene or norbornene derivatives, norbornadiene, dicyclopentadiene, cyclopentene, cycloheptene, cyclooctene, cyclooctadiene or cyclododecene.

The dienes that can be ring-closed using the catalysts prepared in accordance with the invention are described, for example, in Miller et al. [Miller, S. J., Blackwell, H. E., Grubbs, R. H., J. Am. Chem. Soc. 118:9606–9614 (1996)] or in Grubbs et al. [Grubbs, R. H., Miller, S. J., Fu, G. C., Acc. Chem. Res. 28:446–452 (1995)].

The following Examples illustrate the invention in more detail.

EXAMPLE 1

Preparation of $Cl_2[P(iso-C_3H_7)_3]_2Ru=C-CH_2-C_6H_5$ (a) A brown suspension of $RuCl_2$(cis,cis-1,5-cyclooctadiene) (220 mg; 0.78 mmol), 0.22 ml (1.56 mmol) of triethylamine and 0.3 ml of tri-isopropylphosphine in 25 ml of isopropanol is stirred at 80° C. for 15 hours. The resulting clear red solution is cooled to −78° C. After the addition of 0.17 ml of phenylacetylene (1.56 mmol), the solution is warmed to −50° C. over a period of 10 minutes. The resulting dark-brown solution is cooled to −78° C. After the addition of 3 ml of 1M HCl solution in diethyl ether (3 mmol), the temperature is allowed to rise to 0° C. over a period of 15 minutes. The resulting brownish-red suspension is concentrated in vacuo to a brownish-red, semi-solid residue. The residue is stirred with 8 ml of methanol, centrifuged and decanted. The resulting fine residue is stirred with 4 ml of methanol, centrifuged and decanted. By drying in vacuo, 95 mg of the target-compound are obtained in the form of a violet powder (purity: 50%).

(b) A brown suspension of $RuCl_2$(cis,cis-1,5-cyclooctadiene) (110 mg; 0.39 mmol), 0.11 ml (0.78 mmol) of triethylamine and 0.15 ml of tri-isopropylphosphine in 13 ml of isopropanol is stirred at 80° C for 15 hours. The resulting clear red solution is cooled to −78° C. After the addition of 0.8 ml of 1M HCl solution in diethyl ether, stirring is carried out for 5 minutes. After the addition of 0.07 ml of 1-phenylacetylene (0.4 mmol) to the resulting yellow suspension, the temperature is allowed to rise to room temperature over a period of 30 minutes. The resulting brown solution is concentrated under a high vacuum and yields a brownish-red residue. NMR shows the expected product to be almost pure with only traces of by-products.

EXAMPLE 2

Preparation of $Cl_2[P(iso-C_3H_7)_3]_2Ru=CH-C_5H_{11}$ 440 mg of $Cl_2Ru$(cyclooctadiene), 600 μl of tri-isopropylphosphine, 440 μl of triethylamine and 50 ml of isopropanol are placed under nitrogen. The brown suspension is heated to 80° C. After 15 hours at 80° C. the suspension has turned into a clear red solution. 25 ml (0.785 mmol) of that solution are removed and cooled to −78° C. 1.6 ml of 1M HCl solution (2 equivalents) in diethyl ether are added and stirring is carried out at −78° C. for 3 minutes. 180 μl of 1-hexyne are then added and the solution is warmed to −10° C., producing a brownish-violet suspension which is concentrated in vacuo to half its volume. After cooling once more to −25° C., centrifugation and drying of the residue, the title compound is obtained in the form of a dark-violet powder (310 mg/69%).

EXAMPLE 3

Preparation of $Cl_2[P(iso-C_3H_7)_3]_2Ru=CH-C_7H_{15}$ (a) A brown suspension of $RuCl_2$(cis,cis-1,5-cyclooctadiene) (110 mg; 0.39 mmol), 0.11 ml (0.78 mmol) of triethylamine and 0.15 ml of tri-isopropylphosphine in 13 ml of isopropanol is stirred at 80° C. for 15 hours. The resulting clear red solution is cooled to −78° C. After the addition of 0.8 ml of 1M HCl solution in diethyl ether, stirring is carried out for 5 minutes. After the addition of 0.06 ml of 1-octyne (0.8 mmol) to the resulting yellow suspension, the temperature is allowed to rise to room temperature over a period of 15 minutes. The resulting brown solution is concentrated in vacuo and yields a brownish-red residue. The residue is stirred with 2×4 ml of methanol, centrifuged and decanted. The product, a violet powder, is dried in vacuo (yield: 25 mg; 10%).

(b) A brown suspension of $RuCl_2$(cis,cis-1,5-cyclooctadiene) (440 mg; 1.56 mmol), 0.44 ml (3.15 mmol) of triethylamine and 0.6 ml of tri-isopropylphosphine in 50 ml of isopropanol is stirred at 85° C. for 6 hours. The resulting clear red solution is cooled to −78° C. After the addition of 3.2 ml of 1M HCl solution in diethyl ether, stirring is carried out for 5 minutes. After the addition of 0.23 ml of 1-octyne (1.6 mmol) to the resulting yellow suspension, the temperature is allowed to rise to −20° C. The resulting brown suspension is stirred at from −20 to −30° C. for 30 minutes. Concentration at −5° C. under a high vacuum yields a brownish-red residue. The residue is extracted with 25 ml of hexane and yields, after concentration, a brownish-violet, semi-solid residue. The residue is stirred with 20 ml of methanol having a temperature of −70° C., centrifuged and decanted. The fine, dark-violet powder is dried in vacuo. The yield is 270 mg (28%) of pure product.

EXAMPLE 4

Preparation of $Cl_2[P(iso-C_3H_7)_3]_2Ru=CH-CH_3$

A brown suspension of $RuCl_2$(cis,cis-1,5-cyclooctadiene) (110 mg; 0.39 mmol), 0.11 ml of triethylamine and 0.15 ml of tri-isopropylphosphine in 12.5 ml of isopropanol is stirred at 85° C. for 3.5 hours. The resulting clear red solution is cooled to −78° C. After the addition of 0.8 ml of 1M HCl solution in diethyl ether, stirring is carried out for 5 minutes. The resulting yellow suspension is warmed to 10° C. over a period of 30 minutes. By introducing acetylene (2 bubbles/second) a brownish-red suspension is obtained, which is concentrated under a high vacuum. The resulting brownish-red residue is stirred with 4 ml of methanol, centrifuged and decanted. The fine, violet powder is dried in vacuo. The yield is 105 mg (51%) of pure product.

EXAMPLE 5

Preparation of $Cl_2[P(iso-C_3H_7)_3]_2Ru=CH—CH_2C_6H_5$ 440 mg of $Cl_2Ru$(cyclooctadiene), 600 μl of tri-isopropylphosphine, 440 μl of triethylamine and 50 ml of isopropanol are placed under nitrogen. The brown suspension is heated to 85° C. After 3.5 hours at 85° C., the suspension has turned into a red solution. 25 ml (0.785 mmol) of that solution are removed and cooled to −78° C. under nitrogen. 1.58 ml of 1M HCl solution in diethyl ether are added and stirring is carried out for 5 minutes, producing a yellow suspension. Acetylene gas (2 bubbles/second) is then introduced for 30 minutes. A violet precipitate is produced. After the addition of 1.5 ml (15 equivalents) of allyl-benzene, the suspension is warmed to room temperature. After stirring at room temperature for 1 hour, the reaction mixture is concentrated and the residue is washed three times with 8 ml of methanol each time. After drying the residue in vacuo, the title compound is obtained in the form of a violet powder (300 mg/64%).

EXAMPLE 6

Preparation of $Cl_2[P(iso-C_3H_7)_3]_2Ru=CH—C_6H_5$ (a) A brown suspension of $RuCl_2$(cis,cis-1,5-cyclooctadiene) (440 mg; 1.57 mmol), 0.44 ml of triethylamine and 0.6 ml of tri-isopropylphosphine in 50 ml of isopropanol is stirred at 85° C. for 3.5 hours. The resulting clear red solution is cooled to −78° C. After the addition of 3.2 ml of 1M HCl solution in diethyl ether, stirring is carried out for 5 minutes. 0.48 ml of 1-hexyne is added to the resulting yellow suspension. The stir mixture is warmed to −10° C. and stirred for 45 minutes. 3.7 ml of styrene (31 mmol) are added to the resulting brown solution. Stirring for 30 minutes at room temperature and then for 10 minutes at 40° C. results in a brown solution. After concentration under a high vacuum, the residue is stirred with 2×6 ml of methanol, centrifuged and decanted. The fine, violet powder is dried under a high vacuum. The yield is 390 mg (43%) of pure product.

(b) A brown suspension of $RuCl_2$(cis,cis-1,5-cyclooctadiene) (220 mg; 0.78 mmol), 0.22 ml of triethylamine and 0.3 ml of tri-isopropylphosphine in 25 ml of isopropanol is stirred at 95° C. for 3 hours. The resulting clear red solution is cooled to −78° C. After the addition of 1.6 ml of 1M HCl solution in diethyl ether, stirring is carried out for 5 minutes. 0.35 ml of phenylacetylene is added to the resulting yellow suspension. The stir mixture is warmed to −10° C. and stirred for 1 hour. 2 ml of styrene (17 mmol) are added to the resulting violet suspension. Stirring for 1.5 hours at room temperature results in a dark-violet stir mixture, which is concentrated under a high vacuum. The residue is stirred with 5 ml of methanol, centrifuged, decanted, stirred with 2 ml of methanol, centrifuged and decanted. The fine, violet powder is dried under a high vacuum. The yield is 370 mg (81%) of pure product.

EXAMPLE 7

Preparation of $Cl_2[P(iso-C_3H_7)_3]_2Ru=CH—C_6H_4-tert-C_4H_9$

A brown suspension of $RuCl_2$(cis,cis-1,5-cyclooctadiene) (220 mg; 0.78 mmol), 0.22 ml of triethylamine and 0.3 ml of tri-isopropylphosphine in 25 ml of isopropanol is stirred at 95° C. for 3.5 hours. The resulting clear red solution is cooled to −78° C. After the addition of 1.6 ml of 1M HCl solution in diethyl ether, stirring is carried out for 5 minutes. 0.24 ml of 1-hexyne is added to the resulting yellow suspension. The stir mixture is warmed, with stirring, to −15° C. over a period of 15 minutes and to 0° C. over a period of 30 minutes. 1.45 ml of 4-tert-butylstyrene (7.85 mmol) are added to the resulting reddish-brown suspension. Stirring for 20 minutes at room temperature results in a dark-violet solution, which is concentrated under a high vacuum. The resulting dark-violet, liquid mixture consisting of the pure product and 4-tert-butylstyrene may be used, for example, directly in solventless polymerisations of DCPD.

EXAMPLE 8

Preparation of $Cl_2[P(iso-C_3H_7)_3]_2Ru=CH—C_6H_4—CH_3$

A brown suspension of $RuCl_2$(cis,cis-1,5-cyclooctadiene) (110 mg; 0.39 mmol), 0.11 ml of triethylamine and 0.15 ml of tri-isopropylphosphine in 12.5 ml of isopropanol is stirred at 85° C. for 3.5 hours. The resulting clear red solution is cooled to −78° C. After the addition of 0.8 ml of 1M HCl solution in diethyl ether, stirring is carried out for 10 minutes. 0.1 ml of 1-hexyne (0.63 mmol) is added to the resulting yellow suspension. The stir mixture is warmed, with stirring, to −10° C. over a period of 30 minutes and to 0° C. over a period of 15 minutes. 0.42 ml of 4-methylstyrene is added to the resulting violet suspension. Stirring for 30 minutes at room temperature results in a violet solution, which is concentrated under a high vacuum. The resulting violet residue is extracted three times with 15 ml of hexane each time and yields, after concentration, a violet, semi-solid residue. The residue is stirred with 10 ml of methanol having a temperature of 0° C., centrifuged and decanted. The fine, violet powder is dried under a high vacuum. The yield is 105 mg (56%) of pure product.

EXAMPLE 9

Preparation of $Cl_2[P(C_6H_{11})_3]_2Ru=CH—C_6H_5$

A brown suspension of $RuCl_2$(cis,cis-1,5-cyclooctadiene) (440 mg; 1.57 mmol), 0.47 ml of 1,8-diazabicyclo[5.4.0]undec-7-ene (3.14 mmol) and 8 ml of 20% tri-cyclohexylphosphine solution in toluene in 25 ml of isopropanol is stirred at 85° C. for 2 hours. The resulting clear red solution is cooled to 0° C. After the addition of 6.3 ml of 1M HCl solution in diethyl ether to the resulting orange-coloured suspension, stirring is carried out for 10 minutes. 0.48 ml of 1-hexyne is added to the resulting orange-coloured suspension. The stir mixture is warmed to room temperature and stirred for 45 minutes. After the addition of 3.6 ml of styrene (31 mmol), stirring is carried out for 2.5 hours. The resulting violet solution is concentrated. The residue is taken up once more in 25 ml of isopropanol, 4 ml of styrene are added and stirring is carried out for 1 hour. After concentration under a high vacuum, the residue is stirred with 3×8 ml of acetone, centrifuged and decanted. The fine, violet powder is dried under a high vacuum. The yield is 450 mg (35%) of pure product.

EXAMPLE 10

Preparation of $Cl_2[P(iso-C_3H_7)_3]_2Ru=CH-C_6H_5$

A brown suspension of $RuCl_2$(cis,cis-1,5-cyclooctadiene) (5.25 g; 18.7 mmol), 5.25 ml (37.4 mmol) of triethylamine and 7.5 ml of tri-isopropylphosphine in 250 ml of isopropanol is stirred at 80° C. for 3.5 hours. The clear red solution is cooled to −70° C. After the addition of 37.5 ml of 1M HCl solution in diethyl ether, stirring is carried out for 15 minutes. 3.75 ml of 1-pentyne are added to the yellow suspension. The stir mixture is warmed to −10° C. and stirred for 1.5 hours. 21.5 ml of styrene (187 mmol) are added to the resulting violet suspension. Stirring for 1 hour at room temperature produces a dark-violet stir mixture, which is concentrated in vacuo. The residue is stirred with 30 ml of methanol, centrifuged, decanted, stirred with 5 ml of methanol, centrifuged, decanted, and again stirred with 5 ml of methanol, centrifuged and decanted. The fine, violet powder is dried in vacuo. The yield is 7.7 g (71%) of pure product.

EXAMPLE 11

Preparation of $Cl_2[P(C_6H_{11})_3]_2Ru=CH-C_6H_5$

A brown suspension of $RuCl_2$(cis,cis-1,5-cyclooctadiene) (1.32 g; 4.7 mmol), 1.42 ml of 1,8-diazabicyclo[5.4.0] undec-7-ene (9.4 mmol) and 15 ml of 20% tricyclohexylphosphine solution in toluene in 50 ml of isopropanol is stirred at 80° C. for 1 hour. The clear red solution is cooled to 0° C. The addition of 50 ml of tetrahydrofuran produces a clear solution. After the addition of 1.9 ml of 1-pentyne, stirring is carried out for 10 minutes. 9.4 ml of 1M HCl solution in diethyl ether are added to the clear solution. The mixture is warmed to room temperature and stirred for 1.5 hours. 5.4 ml of styrene (47 mmol) are added to the violet suspension. Stirring for 1 hour at room temperature produces a dark-violet stir mixture, which is concentrated in vacuo. The residue is extracted with 30 ml of hexane/$CH_2Cl_2$ (9:1), decanted, and concentrated in vacuo. The residue is stirred with 15 ml of acetone, centrifuged and decanted. The fine, violet powder is dried under a high vacuum. The yield is 1.9 g (49%) of pure product.

What is claimed is:

1. A process for the preparation of a compound of the formula:

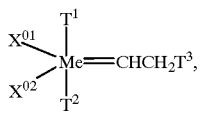

(I)

wherein

Me is ruthenium or osmium;

$X^{01}$ and $X^{02}$ are each independently of the other halogen;

$T^1$ and $T^2$ are each independently of the other a tertiary phosphine or phosphite, or $T^1$ and $T^2$ together are a ditertiary diphosphine or diphosphite; and $T^3$ is hydrogen, $C_1$–$C_{20}$alkyl, $C_3$–$C_8$cycloalkyl, $C_3$–$C_7$heterocycloalkyl having one or two hetero atoms selected from the group oxygen, sulfur and nitrogen, $C_6$–$C_{14}$aryl, or $C_4$–$C_{15}$heteroaryl having from one to three hetero atoms selected from the group oxygen, sulfur and nitrogen, wherein alkyl, cycloalkyl, heterocycloalkyl, aryl and heteroaryl are unsubstituted or substituted by $C_1$–$C_4$alkyl, $C_1$–$C_4$haloalkyl, $C_1$–$C_4$alkoxy, $C_6$–$C_{10}$aryl, $C_6$–$C_{10}$aryloxy, $-NO_2$ or by halogen;

in which a metal salt of the formula:

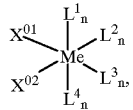

(II)

wherein

Me, $X^{01}$ and $X^{02}$ are as defined above, $L^1$, $L^2$, $L^3$ and $L^4$ are each independently of the others a neutral ligand, and n is 0 or 1;

is first reacted in the presence of a base and a secondary or tertiary alcohol with a tertiary phosphine or phosphite or a ditertiary diphosphine or diphosphite and then reacted in the presence of an acid with an alkyne of the formula:

$$HC\equiv C-T^3, \quad \text{(III)}$$

wherein $T^3$ is as defined above.

2. A process according to claim 1, wherein Me is ruthenium.

3. A process according to claim 1, wherein $X^{01}$ and $X^{02}$ are Cl.

4. A process according to claim 1, wherein the tertiary phosphines or phosphites and the ditertiary diphosphines or diphosphites correspond to formula IV, IVa, IVb or IVc $$PR^1R^2R^3, \quad \text{(IV)}$$

$$R^1R^2P-Z-PR^1R^2, \quad \text{(IVa)}$$

$$P(OR^1)(OR^2)OR^3, \quad \text{(IVb)}$$

$$R^1OP(OR^2)-Z-(OR^2)POR^1, \quad \text{(IVc)}$$

wherein $R^1$, $R^2$ and $R^3$ are each independently of the others $C_1$–$C_{20}$alkyl, $C_4$–$C_{12}$cycloalkyl, $C_2$–$C_{11}$heterocycloalkyl, $C_6$–$C_{16}$aryl, $C_2$–$C_{15}$heteroaryl or $C_7$–$C_{16}$aralkyl, wherein alkyl, cycloalkyl, heterocycloalkyl, aryl, heteroaryl and aralkyl are unsubstituted or substituted by a substituent selected from the group consisting of $C_1$–$C_6$alkyl, $C_1$–$C_6$alkoxy, $C_1$–$C_6$haloalkyl, $C_6$–$C_{16}$aryl, $-NO_2$, $SO_3^-$, ammonium and halogen; the radicals $R^1$ and $R^2$ together are tetra- or penta-methylene which is unsubstituted or substituted by $C_1$–$C_6$alkyl, $C_1$–$C_6$haloalkyl, $-NO_2$ or by $C_1$–$C_6$alkoxy, or are tetra- or penta-methylene which is unsubstituted or substituted by $C_1$–$C_6$alkyl, $C_1$–$C_6$haloalkyl, $-NO_2$ or by $C_1$–$C_6$alkoxy and condensed with one or two 1,2-phenylene(s), and $R^3$ is as defined above; and Z is linear or branched, unsubstituted or $C_1$–$C_4$alkoxy-substituted $C_2$–$C_{12}$alkylene; unsubstituted or $C_1$–$C_4$alkyl- or $C_1$–$C_4$alkoxy-substituted 1,2- or 1,3-cycloalkylene having from 4 to 8 carbon atoms; unsubstituted or $C_1$–$C_4$alkyl- or $C_1$–$C_4$alkoxy-substituted 1,2- or 1,3-heterocycloalkylene having 5 or 6 ring members and one hetero atom from the group O atom and N atom, unsubstituted or $C_1$–$C_4$alkyl- or $C_1$–$C_4$alkoxy-substituted 1,2-phenylene; 1-methylene-phen-2-yl; 1,2-dimethylenebenzene or unsubstituted or $C_1$–$C_4$alkyl- or $C_1$–$C_4$alkoxy-substituted 2,2'-biphenylene.

5. A process according to claim 1, wherein $T^1$ and $T^2$ correspond to a tertiary phosphine of formula IV wherein $R^1$, $R^2$ and $R^3$ are each independently of the others $C_1$–$C_{20}$-alkyl, $C_4$–$C_{12}$cycloalkyl or $C_6$–$C_{16}$aryl, wherein alkyl, cycloalkyl and aryl are unsubstituted or substituted by a substituent selected from the group consisting of $C_1$–$C_6$alkyl, $C_1$–$C_6$alkoxy, $C_1$–$C_6$haloalkyl, $C_6$–$C_{16}$aryl, —$NO_2$, $SO_3^-$, ammonium and halogen.

6. A process according to claim 5, wherein $T^1$ and $T^2$ are $(C_6H_5)_2(iso$-$C_3H_7)P$, $(C_6H_5)(iso$-$C_3H_7)_2P$, $(C_6H_5)_2(C_6H_{11})P$, $(C_6H_5)_3P$, $(C_6H_5CH_2)_3P$, $(C_5H_9)_3P$, $(2,3$-di-tert-$C_4H_9$—$C_6H_3)_3P$, $(2,6$-di-tert-$C_4H_9$–$C_6H_3)_3P$, $(3$-$CH_3$-$6$-tert-$C_4H_9$—$C_6H_3)_3P$, $(C_6H_{11})_3P$, $(2$-$CH_3$-$6$-tert-$C_4H_9$—$C_6H_3)_3P$, $(4$-tert-$C_4H_9$—$C_6H_4)_3P$, $(3$-tert-$C_4H_9$—$C_6H_4)_3P$, $(2$-tert-$C_4H_9$—$C_6H_4)_3P$, $(4$-iso-$C_4H_9$—$C_6H_4)_3P$, $(CH_3)_3P$, $(C_2H_5)_3P$, $(n$-$C_3H_7)_3P$, $(iso$-$C_3H_7)_3P$, $(n$-$C_4H_9)_3P$, $(3$-iso-$C_4H_9$—$C_6H_4)_3P$, $(2$-iso-$C_4H_9$—$C_6H_4)_3P$, $(4$-n-$C_4H_9$—$C_6H_4)_3P$, $(3$-n-$C_4H_9$—$C_6H_4)_3P$, $(sec$-$C_4H_9)_3P$, $(2$-$CH_3$—$C_6H_4)_3P$, $(3$-$CH_3$—$C_6H_4)_3P$, $(4$-$CH_3$—$C_6H_4)_3P$, $(2,4$-di-$CH_3$—$C_6H_3)_3P$, $(2,6$-di-$CH_3$-$C_6H_3)_3P$; $(2$-$C_2H_5$—$C_6H_4)_3P$, $(3$-$C_2H_5$—$C_6H_4)_3P$, $(4$-$C_2H_5$—$C_6H_4)_3P$, $(2$-n-$C_3H_7$—$C_6H_4)_3P$, $(3$-n-$C_3H_7$—$C_6H_4)_3P$, $(4$-n-$C_3H_7$—$C_6H_4)_3P$, $(2$-iso-$C_3H_7$—$C_6H_4)_3P$, $(3$-iso-$C_3H_7$—$C_6H_4)_3P$, $(4$-iso-$C_3H_7$—$C_6H_4)_3P$, $(C_6H_5)(C_6H_{11})_2P$, $(2$-n-$C_4H_9$—$C_6H_4)_3P$, $(C_6H_5)(sec$-$C_4H_9)_2P$, $(C_6H_{11})[C(C_2H_4)_2(N(CH_3)_3Cl)]P$, $(C_6H_{11})_2[CH_2CH_2N(CH_3)_3Cl]P$, $(C_6H_{11})_2[CH_2CH_2SO_3Na]P$ or $(2,4$di-tert-$C_4H_9$—$C_6H_3)_3P$.

7. A process according to claim 1, wherein $T^3$ is hydrogen, $C_1$–$C_9$alkyl, cyclopentyl, cyclohexyl, phenyl, benzyl or naphthyl, which are unsubstituted or substituted by $C_1$–$C_4$alkyl, $C_1$–$C_4$alkoxy, $C_1$–$C_4$haloalkyl, phenyl, F or by Cl.

8. A process according to claim 1, wherein the compounds of formulae I are those of formulae Ib

wherein

Me is Ru or Os, $R^5$ is α-branched $C_3$–$C_8$alkyl, or $C_5$–$C_8$cycloalkyl which is unsubstituted or substituted by $C_1$–$C_4$alkyl, $C_1$–$C_4$haloalkyl, $C_1$–$C_4$alkoxy, halogen or by —$NO_2$, or $C_6$–$C_{10}$aryl which is unsubstituted or substituted by $C_1$–$C_4$alkyl, $C_1$–$C_4$haloalkyl, $C_1$–$C_4$alkoxy, halogen or by —$NO_2$, and $T^3$ is hydrogen, $C_1$–$C_6$alkyl, or $C_5$–$C_8$cycloalkyl which is unsubstituted or substituted by $C_1$–$C_4$alkyl, $C_1$–$C_4$haloalkyl, $C_1$–$C_4$alkoxy, halogen or by —$NO_2$, or $C_6$–$C_{10}$aryl which is unsubstituted or substituted by $C_1$–$C_4$alkyl, $C_1$–$C_4$haloalkyl, $C_1$–$C_4$alkoxy, halogen or by —$NO_2$.

9. A process according to claim 1, wherein the compounds of formulae I are $Cl_2[P(C_5H_9)_3]_2Me$=$CH$—$CH_3$, $Cl_2[P(C_6H_{11})_3]_2Me$=$CHCH_3$, $Cl_2[P(C_5H_9)_3]_2Me$=$CH$-n-$C_4H_9$, $Cl_2[P(C_6H_{11})_3]_2Me$=$CH$-n-$C_4H_9$, $Br_2[P(C_5H_9)_3]_2Me$=$CH$—$CH_2C_6H_5$, $BrCl[P(C_6H_{11})_3]_2Me$=$CH$—$CH_2C_6H_5$, or $BrCl[P(iso$-$C_3H_7)_3]_2Me$=$CH$—$CH_2C_6H_5$, wherein Me is Os or Ru.

\* \* \* \* \*